US011470857B2

(12) United States Patent
Christensen et al.

(10) Patent No.: US 11,470,857 B2
(45) Date of Patent: Oct. 18, 2022

(54) METHOD OF PRODUCING BETA-CASEIN COMPOSITIONS AND RELATED PRODUCTS

(71) Applicant: ARLA FOODS AMBA, Viby J (DK)

(72) Inventors: Jesper Christensen, Silkeborg (DK); Hans Henrik Holst, Videbæk (DK)

(73) Assignee: ARLA FOODS AMBA, Viby J (DK)

( * ) Notice: Subject to any disclaimer, the term of this patent is extended or adjusted under 35 U.S.C. 154(b) by 707 days.

(21) Appl. No.: 14/763,141

(22) PCT Filed: Jan. 23, 2014

(86) PCT No.: PCT/EP2014/051315
§ 371 (c)(1),
(2) Date: Jul. 23, 2015

(87) PCT Pub. No.: WO2014/114709
PCT Pub. Date: Jul. 31, 2014

(65) Prior Publication Data
US 2015/0359244 A1 Dec. 17, 2015

Related U.S. Application Data

(60) Provisional application No. 61/755,732, filed on Jan. 23, 2013.

(30) Foreign Application Priority Data

Jan. 23, 2013 (EP) .................... 13152410

(51) Int. Cl.
*A23J 1/20* (2006.01)
*A23C 9/142* (2006.01)
(Continued)

(52) U.S. Cl.
CPC ............... *A23J 1/202* (2013.01); *A23C 9/142* (2013.01); *A23C 9/1422* (2013.01); *A23J 3/10* (2013.01);
(Continued)

(58) Field of Classification Search
CPC .... A23J 1/20; A23J 1/202; A23J 1/207; A23J 3/10; A23C 9/14; A23C 9/1422;
(Continued)

(56) References Cited

U.S. PATENT DOCUMENTS 5,169,666 A 12/1992 Woychik
5,397,577 A 3/1995 Le Magnen et al.
(Continued)

FOREIGN PATENT DOCUMENTS

BY 15386 2/2012
CA 2629427 C 12/2013
(Continued)

OTHER PUBLICATIONS

European Extended Search Report for Application No. 16205408.4 dated Apr. 7, 2017 (11 pages).
(Continued)

*Primary Examiner* — Lien T Tran
*Assistant Examiner* — Tynesha L McClain
(74) *Attorney, Agent, or Firm* — Casimir Jones SC; Lisa Mueller

(57) ABSTRACT

The present invention pertains to a method of producing beta-casein-containing compositions and products obtainable by such methods. More particularly, the invention pertains to a method of producing beta-casein compositions using controlled microfiltration first at a temperature higher than 20 degrees C., followed by cooling of the retentate to 0-15 degrees C. and a second microfiltration of the cooled composition resulting in beta-casein containing permeate.

20 Claims, 5 Drawing Sheets

(51) Int. Cl.
A23J 3/10 (2006.01)
C07K 1/34 (2006.01)
C07K 14/47 (2006.01)

(52) U.S. Cl.
CPC .......... C07K 1/34 (2013.01); C07K 14/4732 (2013.01); *A23C 2210/206* (2013.01); *A23V 2002/00* (2013.01); *A23V 2200/00* (2013.01)

(58) Field of Classification Search
CPC .. A23C 2210/206; C07K 14/473; C07K 1/34; A23L 33/19
See application file for complete search history.

(56) References Cited

U.S. PATENT DOCUMENTS

| | | | |
|---|---|---|---|
| 11,219,225 | B2 | 1/2022 | Ur-Rehman et al. |
| 2007/0104847 | A1 | 5/2007 | O'Mahony |
| 2014/0057040 | A1 | 2/2014 | van der Padt et al. |

FOREIGN PATENT DOCUMENTS

| | | | | |
|---|---|---|---|---|
| FR | 2 592 769 | A1 | | 7/1987 |
| FR | 2 809 595 | B1 | | 12/2001 |
| NL | 2 006 662 | C | | 10/2012 |
| RU | 1824700 | | | 4/1996 |
| WO | 1992/000017 | A1 | | 1/1992 |
| WO | 9406306 | A1 | | 3/1994 |
| WO | 1994/013148 | A1 | | 6/1994 |
| WO | WO 02069724 | A1 | * | 9/2002 ............. A01J 11/04 |
| WO | 2007100264 | A1 | | 9/2007 |
| WO | 2008079031 | A2 | | 7/2008 |
| WO | 2008127104 | A1 | | 10/2008 |
| WO | WO 2012/148269 | A1 | | 11/2012 |
| WO | 2013/068653 | A2 | | 5/2013 |
| WO | 2014/114709 | A2 | | 7/2014 |

OTHER PUBLICATIONS

Hekken et al., Lait, 80: 69-76 (2000), Title: Use of Cold Microfiltration to Produce unique beta-casein enriched milk gels.
International Preliminary Report on Patentability mailed in International Patent Application No. PCT/EP2014/051315 (dated May 2015).
International Search Report mailed in International Patent Application No. PCT/EP2014/051315 (dated Jul. 2014).
Ono et al., Agric. Biol. Chem., 54(6): 1385-1392 (1990), Title: Changes in the Protein Composition and Size Distribution of Bovine Casein Micelles Induced by Cooling.
Russian Patent Office Action and Search Report for Application No. 2015134776 dated Dec. 7, 2017, with English translation, 17 pages.
Pouliot et al., "Study of the dissociation of β-casein from native phosphocaseinate," Lait, 1994, 74, 325-332.
Walstra et al., "Dairy Science and Technology," 2nd Edition, 2006, pp. 146-147.
Davies et al., "Variation in the protein composition of bovine casein micelles and serum casein in relation to micellar size and milk temperature," Journal of Dairy Research, 1983, 50, 67-75.
Van Hekken et al., "Use of cold microfiltration to produce unique β-casein enriched milk gels," Lait, 2000, 80, 69-76.
Letter of Patentee to EPO regarding Application No. PCT/EP2014/051315 dated Dec. 23, 2014 (2 pages).
Pierre et al., "Préparation de phosphocaséinate natif par microfiltration sur membrane," Lait, 1992, 72, 461-474.
Saboya et al., "Current development of microfiltration technology in the dairy industry," Lait, 2000, 80, 541-553.
Britz et al., "Advanced Dairy Science and Technology," 2008.
Notice of Opposition to European Patent No. 2947996 dated Sep. 21, 2017 (15 pages).
O. Le Berre & G. Daufin, "Skimmilk crossflow microfiltration performance versus permeation flux to wall shear stress ration." J. Membrane Science 1996, 117:261-270.
Opponent's submission filed Nov. 21, 2018 in opposition of EP Patent 2947996, 4 pages.
Office Action dated Apr. 4, 2019, European Application No. 16205408. 4, 7 pages.
Nelson et al., "A microfiltration Process to Maximize Removal of Serum Proteins from Skim Milk Before Cheese Making." J Dairy Sci. 2005, 88 1891-1900.
Bobe et al.; "Separation and Quantification of Bovine Milk Proteins by Reversed-Phase High-Performance Liquid Chromatography," J Agric Food Chem. Feb. 16, 1998;46(2):458-463).
Nielsen, Werner Kofod, "Membrane filtration and related molecular separation technologies", APV Systems, 2000, ISBN 87-88016757, pp. 2-195.
Tetra Pak, "Dairy processing Handbook", 2003, (ISBN 91-631-3427-6), Index only.
Turhan et al., "Fractionation of Caseins by Anion-exchange Chromatography Using Food-grade Buffers," J Food Science,vol. 69, Nr. 5, 2003, Institute of Food Technologists.

* cited by examiner

METHOD OF PRODUCING BETA-CASEIN COMPOSITIONS AND RELATED PRODUCTS

CROSS-REFERENCE TO RELATED APPLICATIONS

This is a U.S. national stage entry of International Patent Application No. PCT/EP2014/051315, filed on Jan. 23, 2014, which claims priority to U.S. Provisional Patent Application No. 61/755,732, filed on Jan. 23, 2013, and European Patent Application No. 13152410.0, filed on Jan. 23, 2013, the entire contents of all of which are fully incorporated herein by reference

FIELD OF THE INVENTION

The present invention pertains to a method of producing beta-casein-containing compositions and products obtainable by such methods. More particularly, the invention pertains to a method of producing beta-casein compositions using controlled microfiltration.

BACKGROUND OF THE INVENTION

Beta-casein is the major protein found in human milk. The protein binds to calcium at its phosphorylated regions. The protein, as a whole, is disordered and is characterized as a random coil protein.

Beta-casein is also found in bovine milk, however, in a lower concentration than in human milk. At room temperature, bovine beta-casein is bound to the casein micelles of bovine milk, but at lower temperatures, e.g. 2-5 degrees C., beta-casein is known to dissociate partly from the casein micelles to form free beta-casein, e.g. in the form of single free beta-casein molecules or small beta-casein aggregates.

PRIOR ART

Several approaches for isolating beta-casein from milk have been described in the prior art.

FR 2,592,769 A discloses production of beta-casein by microfiltration of a cooled liquid feed containing calcium aggregated caseinate.

U.S. Pat. No. 5,169,666 A describes a process for producing a beta-casein enriched milk protein product by subjecting a cooled skimmed milk to microfiltration. The used MF filter has a pore size of 0.1-0.2 micrometer.

US2007104847A discloses a method of producing beta-casein: The method is based on initial cold microfiltration of cooled skimmed milk to obtain a partly beta-casein depleted retentate and a permeate containing milk serum protein and a significant amount of beta-casein. The beta-casein containing permeate may be subjected to further purification.

WO 2012/148,269 A1 discloses a method of preparing milk protein fraction, including beta-casein, using a first microfiltration step and subjecting the retentate of the first microfiltration step to a second microfiltration. The first microfiltration step may be performed at a warm temperature and the second microfiltration step may be performed at a cold temperature.

SUMMARY OF THE INVENTION

An aspect of the invention pertains to a method of producing a beta-casein-containing composition, the method comprising the steps of:

a) pre-heating a milk by adjusting it to a pre-heating temperature ($T_{pre}$) of at least 20 degrees C., thereby providing a warm milk, b) subjecting the warm milk to microfiltration (MF), thereby providing a first MF permeate and a first MF retentate, c) optionally, subjecting the first MF retentate to MF-diafiltration, d) adjusting the temperature of a first composition derived from the first MF retentate to a cold temperature ($T_{old}$) in the range of 0-15 degrees C. and keeping the temperature of the first composition within that range for a duration ($t_{cold}$) of at least 0.5 hour, thereby obtaining a cooled first composition, e) subjecting the cooled first composition to microfiltration, thereby obtaining a second retentate and a second permeate, which second permeate is enriched with respect to beta-casein, and f) optionally, subjecting the second MF retentate to MF-diafiltration, g) optionally, subjecting a second composition derived from the second permeate to one or more further processing steps, e.g. further purification and/or concentration steps, thereby providing the beta-casein-containing composition.

The second permeate of step e) may for example be used as the beta-casein-containing composition. Alternatively, a combination of the second permeate of step e) and subsequent permeates of the MF-diafiltration of step f) may be used as the beta-casein-containing composition. Alternatively, the product resulting from step g) may be used as the beta-casein-containing composition.

As steps c), f) and g) are deemed optional, there are several variants to the method. The method may e.g. comprise the steps a), b), d), and e). Alternatively, the method may comprise the steps a), b), c), d), and e). For example, the method may comprise the steps a), b), d), e), and f). The method may e.g. comprise the steps a), b), d), e), and g). Alternatively, the method may comprise the steps a), b), d), e), f), and g). For example the method may comprise the steps a), b), c), d), e), and f). In other embodiments, the method comprises the steps a), b), c), d), e), and g). The method may e.g. comprise the steps a), b), c), d), e), f), and g).

In some embodiments of the invention, the method consists of the steps a), b), d), and e). Alternatively, the method may consist of the steps a), b), c), d), and e). For example, the method may consist of the steps a), b), d), e), and f). The method may e.g. consist of the steps a), b), d), e), and g). Alternatively, the method may consist of the steps a), b), d), e), f), and g). For example the method may consist of the steps a), b), c), d), e), and f). In other embodiments, the method consists of the steps a), b), c), d), e), and g). The method may e.g. consist of the steps a), b), c), d), e), f), and g).

An exemplary embodiment of the invention is illustrated in FIG. 1. Here the milk (1) contacts a heating unit (2) which adjusts the temperature of the milk to the pretreatment temperature ($T_{pre}$). The milk is held at $T_{pre}$ for a duration, $t_{pre}$, sufficient to allow at least a substantial part of the free beta-casein to bind to the casein micelles.

The warm milk is then transferred to a first microfiltration unit (3) and is separated into a first permeate (6) and a first retentate (5). This embodiment involves subsequent diafiltration of the first retentate (4), which is mixed with a diluent (5), and the resulting mixture is then transferred to yet a microfiltration unit (3'), resulting in a first MF-diafiltration retentate (4') and a first MF-diafiltration permeate (6'). Yet a step of MF-diafiltration is performed on the first MF-diafiltration retentate (4'). The temperature during the warm microfiltration, $T_{wMF}$, may be the same as or different from $T_{pre}$, though is it preferred that $T_{wMF}$ is at least 20 degrees C.

Subsequently, the resulting retentate (4") is diluted and transferred to a cooling unit where the diluted retentate is cooled to the temperature $T_{cold}$. The diluted retentate is kept at a cold temperature for a duration, $t_{cold}$, sufficient to dissociate a significant part of the casein-micelle-bound beta-casein, thereby providing a substantial part of free beta-casein in the cooled, diluted retentate. The free beta-casein is separated from the cooled, diluted retentate by cold MF (8) and cold MF-diafiltration (8' and 8"). The free beta-casein moves through the MF filter and into the permeate streams (10, 10', 10") which are combined and transferred to a spray-drying system (12), which converts the combined permeates to a beta-casein-containing powder.

The permeates of the warm MF/MF-diafiltration (6, 6', 6") contain high quality serum protein and may be converted into powder or liquid form serum protein concentrates.

The retentate stream (9") leaving the cold MF/MF-diafiltration is a partly beta-casein depleted isolate of micellar casein and may e.g. be used as a food additive or in the production of cheese.

Yet an aspect of the invention pertains to a beta-casein-containing composition obtainable by a method according to any of the preceding claims.

DETAILED DESCRIPTION OF THE INVENTION

Figure 1:
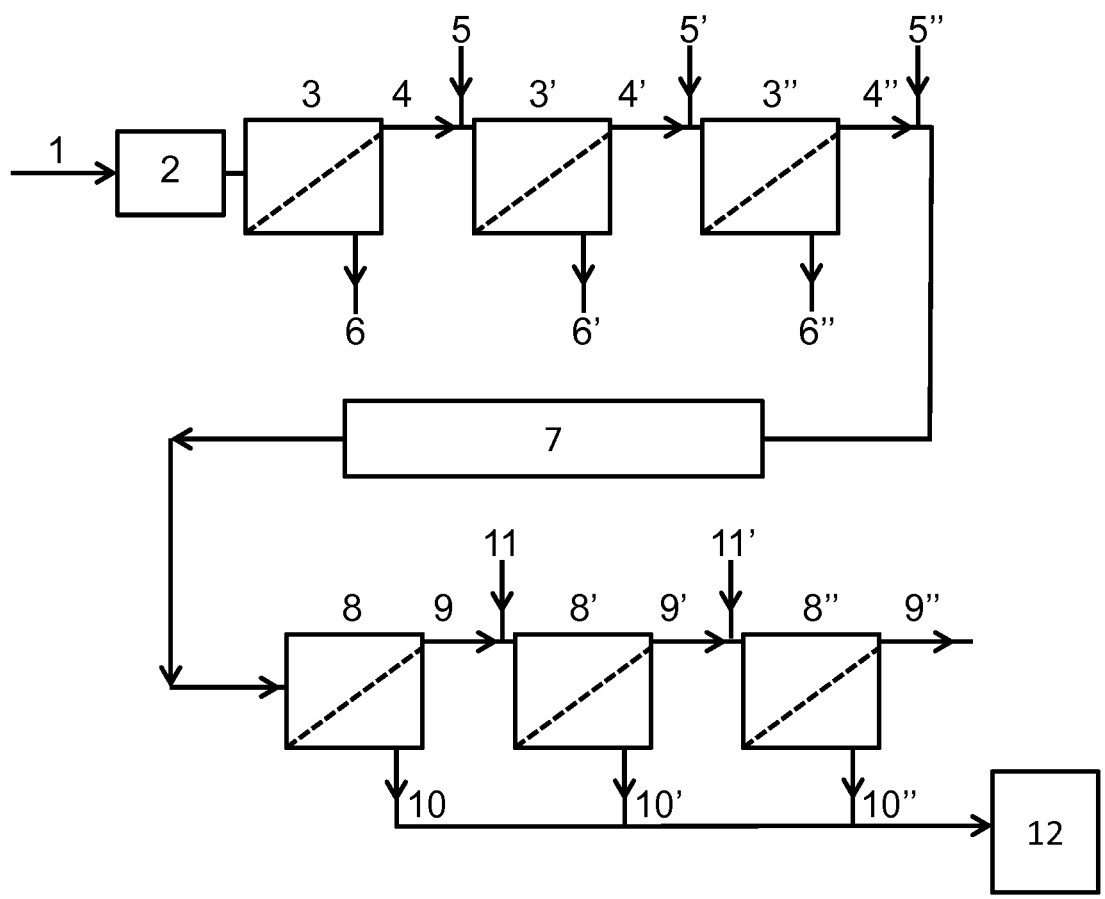
FIG. 1 is a schematic illustration of an exemplary embodiment of the invention, where (1) is the milk, (2) is the pre-heating unit, 3/3'/3" are MF units, 4/4'/4" are retentate streams, 5/5'/5" are additions of the first diluent, 6/6'/6" are permeate streams, (7) is the cooling and holding of the diluted retentate (4"), 8/8'/8" are MF units, 9/9'/9" are retentate streams, 10/10'/10" are permeate streams, 11/11' are additions of the second diluent, (12) is a spray-drying unit.

As said, an aspect of the invention pertains to a method of producing a beta-casein-containing composition, the method comprising the steps of:

a) pre-heating a milk by adjusting it to a pre-heating temperature ($T_{pre}$) of at least 20 degrees C., thereby providing a warm milk, b) subjecting the warm milk to microfiltration (MF), thereby providing a first MF permeate and a first MF retentate, c) optionally, subjecting the first MF retentate to MF-diafiltration, d) adjusting the temperature of a first composition derived from the first MF retentate to a cold temperature ($T_{cold}$) in the range of 0-15 degrees C. and keeping the temperature of the first composition within that range for a duration ($t_{cold}$) of at least 0.5 hour, thereby obtaining a cooled first composition, e) subjecting the cooled first composition to microfiltration, thereby obtaining a second retentate and a second permeate, which second permeate is enriched with respect to beta-casein, and f) optionally, subjecting the second MF retentate to MF-diafiltration, g) optionally, subjecting a second composition derived from the second permeate to one or more further processing steps, e.g. further purification and/or concentration steps, thereby providing the beta-casein-containing composition.

The beta-casein-containing composition obtainable by the method of the invention preferably contains at least 30% (w/w) beta-casein relative to the total amount of protein. For example, the beta-casein-containing composition may contain at least 50% (w/w) beta-casein relative to the total amount of protein. The beta-casein-containing composition may contain at least 60% (w/w) beta-casein relative to the total amount of protein. Alternatively, the beta-casein-containing composition may contain at least 70% (w/w) beta-casein relative to the total amount of protein, such as e.g. at least 80% (w/w) beta-casein.

In some preferred embodiments of the invention, the beta-casein-containing composition contains an amount of beta-casein in the range of 30-100% (w/w) relative to the total amount of protein. For example, the beta-casein-containing composition may contain an amount of beta-casein in the range of 50-95% (w/w) relative to the total amount of protein. The beta-casein-containing composition may e.g. contain an amount of beta-casein in the range of 55-90% (w/w) relative to the total amount of protein. Alternatively, the beta-casein-containing composition may contain an amount of beta-casein in the range of 60-80% (w/w) relative to the total amount of protein.

The beta-casein containing composition of the invention preferably contains at least 50% (w/w) beta-casein relative to the total amount of casein. For example, the beta-casein-containing composition may contain at least 70% (w/w) beta-casein relative to the total amount of casein. The beta-casein-containing composition may contain at least 80% (w/w) beta-casein relative to the total amount of casein. Alternatively, the beta-casein-containing composition may contain at least 90% (w/w) beta-casein relative to the total amount of casein. For example, the beta-casein-containing composition may contain at least 95% (w/w) beta-casein relative to the total amount of casein, such as e.g. at least 97% (w/w) beta-casein.

The method may also be used for producing a serum protein concentrate, e.g. by collecting the first permeate and/or additional permeates from MF-diafiltration of the first retentate. Additionally, the method may be used for producing a beta-casein depleted micellar casein isolate, e.g. by collecting the second retentate and/or a subsequent retentate obtained by subjecting the second retentate to cold MF-diafiltration. For example, the method may be used for producing a beta-casein-containing composition, a serum protein concentrate, and a beta-casein reduced micellar casein isolate.

In the context of the present invention, the phrase "Y and/or X" means "Y" or "X" or "Y and X". Along the same line of logic, the phrase "$n_1, n_2, \ldots, n_{i-1}$, and/or $n_i$" means "$n_1$" or "$n_2$" or ... or "$n_{i-1}$" or "$n_i$" or any combination of the components $n_1, n_2, \ldots n_{i-1}$, and $n_i$.

In the context of the present invention, the term "casein micelle" pertains to a spherical aggregate of casein species, such as alpha-s1-casein, alpha-s2-casein, beta-casein and kappa-casein. The casein species of the micelle are typically held together by calcium ions and hydrophobic interactions. Most of the casein of native milk is present in the form of casein micelles.

The human version of beta-casein is the major protein found in human milk. In bovine milk, however, the bovine version of beta-casein only constitutes approx. 28-32% (w/w) of the total amount of protein. The beta-casein molecule binds to calcium at its phosphorylated regions, which are highly conserved. Beta-casein may e.g. be present in the form of casein-micelle-bound beta-casein or in the form of free beta-casein. The term "free beta-casein" refers to casein which is not bound to the casein micelles. Free beta-casein may for example be free molecules of beta-casein or so-called sub-micelles, which primarily contains a number of associated beta-caseins.

As said, step a) of the method involves adjusting the temperature of a milk to a pre-heating temperature ($T_{pre}$) of at least 20 degrees C., thereby providing a warm milk. Step a) may be perceived as a step of pre-heating the milk before the milk contacts the micro filtration filter.

The milk provided in step a) is preferably a liquid milk obtained from a mammal. As used herein the term "milk" includes raw milk, whole milk, skim milk, fat-free milk, low fat milk, and full fat milk. The term milk furthermore includes fresh milk or milk based on milk powder resuspended in water.

The solid contents of the milk may e.g. have been modified by dilution or concentration, i.e. the milk may e.g. be a concentrated milk or a diluted milk.

Fat-free milk is a non-fat or skim milk product. Low-fat milk is typically defined as milk that contains from about 1% to about 2% fat. Full fat milk often contains about 3.25% fat.

Sources of milk include, but are not limited to, cow, sheep, goat, buffalo, camel, llama, mare and deer.

In some preferred embodiments of the invention, the milk comprises, or even consists of, bovine milk.

In some embodiments of the invention, the milk has been subjected to pasteurisation and/or bactofugation to eliminate, or at least reduce, the microbial load of the milk.

In some preferred embodiments of the invention, the milk of a) comprises 1-4.5% w/w casein, 0.1-1% w/w milk serum protein, and 0.001-4% w/w milk fat. In even more preferred embodiments of the invention, the milk of step a) comprises 2-4.5% w/w casein, 0.2-1% w/w milk serum protein, and 0.01-0.5% w/w milk fat.

While in theory all types of mammal milk may be used, it is particularly preferred that the milk has recently been milked from the source of the milk, e.g. from cows. For example, the milk may be at most 5 days old, i.e. at most 5 days since milking. Preferably, the milk is at most 4 day old. For example, the milk may be at most 3 days old. Even more preferably, the milk is at most 2 days old. For example, the milk may be at most 1 day old.

The use of newly milked milk for the present method is advantageous as it results in less degradation of beta-casein and therefore a better beta-casein yield than older milk.

The pre-heating temperature, $T_{pre}$, is at least 20 degrees C. For example, $T_{pre}$ may be at least 30 degrees C. Alternatively, $T_{pre}$ may be at least 40 degrees C. $T_{pre}$ may e.g. be at least 50 degrees C.

Even higher pre-heating temperatures may be desired, thus, $T_{pre}$ may be at least 60 degrees C. For example, $T_{pre}$ may be at least 70 degrees C. Alternatively, the $T_{pre}$ may be at least 80 degrees C. $T_{pre}$ may e.g. be at least 100 degrees C.

In some embodiments of the invention, $T_{pre}$ is in the range of 20-180 degrees C. For example, $T_{pre}$ may be in the range of 20-60 degrees C. Alternatively, $T_{pre}$ may be in the range of 60-120 degrees C. In some embodiments $T_{pre}$ is in the range of 120-180 degrees C.

The duration of the pre-heating, $t_{pre}$, may be varied depending on the pre-heating temperature, $T_{pre}$, used in the process. It is, however, preferred that the milk is sufficiently pre-heated to allow for association of free beta-casein to the casein micelles.

The present inventors have seen indications that a too short heat pre-treatment time and/or a too low pre-treatment temperature lead to a reduced yield of beta-casein. The inventors have discovered that it is possible to increase the yield of beta-casein by controlling $t_{pre}$ and $T_{pre}$.

The higher temperatures used during the pre-heating, the shorter heating times are required to provide an efficient re-association of free beta-casein to the casein micelles. If $T_{pre}$ is in the range of 20-60 degrees C., the holding time may e.g. be in the range of 1 minute-1 hour. If $T_{pre}$ is in the range of 60-120 degrees C., the holding time may e.g. be in the range of 0.5 second-5 minutes. If $T_{pre}$ is in the range of 120-180 degrees C., the holding time may e.g. be in the range of 0.05 second-4 seconds.

In some embodiments of the invention, $T_{pre}$ is in the range of 20-60 degrees C., the holding time may e.g. be in the range of 1 minute-1 hour.

The warm milk may furthermore contain the usual carbohydrates, fat and minerals found in mammal milk.

In the context of the present invention, the terms "method" and "process" are used interchangeably.

In some preferred embodiments of the invention the temperature of the milk is kept within the pre-heating temperature range for a duration, $t_{pre}$, of most 24 hours. Alternatively, $t_{pre}$ may be at most 5 hours. $t_{pre}$ may for example be at most 1 hour. For example, $t_{pre}$ may be at most 0.5 hour.

The pre-heating temperature range is the temperature range in which the milk is pre-heated before it contacts the MF filter in step b).

Even shorter $t_{pre}$ may be used, for example if the pre-heating temperature is relatively high. Thus, in some embodiments of the invention, $t_{pre}$ is at most 30 minutes. Alternatively, $t_{pre}$ may by at most 10 minutes, or even shorter such as at most 5 minutes.

A very short $t_{pre}$ may be used, e.g. when $T_{pre}$ exceeds 60 degrees C. Thus, in some embodiments of the invention, $t_{pre}$ is at most 1 minute. Alternatively, $t_{pre}$ may by at most 0.5 minute, or even shorter such as at most 0.1 minute.

For example, the milk maybe kept within the pre-heating temperature range for a duration, $t_{pre}$, in the range of 1 second-24 hours. Alternatively, $t_{pre}$ may be in the range of 10 second-5 hours. $t_{pre}$ may for example be in the range of 30 seconds-1 hour. For example, $t_{pre}$ may be in the range of 1 minute-0.5 hour.

As said, relatively short $t_{pre}$ may be used, for example if the pre-heating temperature is relatively high. Thus, in some embodiments of the invention, $t_{pre}$ is in the range of 1 second-30 minutes. Alternatively, $t_{pre}$ may be in the range of 10 seconds-10 minutes. $t_{pre}$ may e.g. be in the range of 20 seconds-5 minutes.

In some embodiments of the invention, the pre-heating temperature range is 40-60 degrees C. and $t_{pre}$ is at most 2 hours. For example, the pre-heating temperature range may be 40-60 degrees C. and $t_{pre}$ may be at most 0.5 hour. The pre-heating temperature range may e.g. be 40-60 degrees C. and $t_{pre}$ may be at most 0.2 hour. Alternatively, the pre-heating temperature range may e.g. be 40-60 degrees C. and $t_{pre}$ may be at most 0.1 hour.

In other embodiments of the invention, the pre-heating temperature range is 60-120 degrees C. and $t_{pre}$ is at most 0.2 hours. For example, the pre-heating temperature range may be 60-120 degrees C. and $t_{pre}$ may be at most 2 minutes. The pre-heating temperature range may e.g. be 60-120 degrees C. and $t_{pre}$ may be at most 30 seconds. Alternatively, the pre-heating temperature range may e.g. be 60-120 degrees C. and $t_{pre}$ may be at most 10 seconds.

In yet other embodiments of the invention, the pre-heating temperature range is 120-180 degrees C. and $t_{pre}$ is at most 20 second. For example, the pre-heating temperature range may be 120-180 degrees C. and $t_{pre}$ may be at most 2 seconds. The pre-heating temperature range may e.g. be 120-180 degrees C. and $t_{pre}$ may be at most 0.5 seconds. Alternatively, the pre-heating temperature range may e.g. be 120-180 degrees C. and $t_{pre}$ may be at most 0.2 seconds.

Step b) involves subjecting the warm milk to microfiltration, thereby providing a first MF permeate and a first MF retentate.

The MF of step b) is performed using a filter that retains at least a substantial fraction of the casein micelles, and preferably substantially all, but allows for the passage of milk serum protein.

The pre-heating of the milk performed during step a) results in binding of a major part, and preferably substantially all, of the available beta-casein to the casein micelles.

In some preferred embodiments of the invention the filter for warm MF has a nominal pore size in the range of 0.005-0.3 micrometer. For example, the filter for warm MF may have a nominal pore size in the range of 0.007-0.2 micrometer. Alternatively, the filter for warm MF may have a nominal pore size in the range of 0.01-0.1 micrometer. The filter for warm MF may e.g. have a nominal pore size in the range of 0.01-0.05 micrometer.

In some preferred embodiments of the invention, the MF filter is used in cross-flow mode.

A suitable microfiltration system can e.g. be found in Tetra Pak Dairy processing Handbook 2003 (ISBN 91-631-3427-6), which is incorporated herein by reference for all purposes.

More details regarding the implementation of microfiltration and MF-diafiltration can be found in the books "Tetra Pak Dairy processing Handbook", 2003, (ISBN 91-631-3427-6) and "Membrane filtration and related molecular separation technologies", Werner Kofod Nielsen, APV Systems, 2000, ISBN 87-88016757, which are incorporated herein by reference for all purposes.

In some preferred embodiments of the invention the method of the present invention comprises step c), i.e. a step of subjecting the first retentate to MF-diafiltration.

The present inventors have found that the use of diafiltration in connection with the first microfiltration step is advantageous as it allows for washing away serum protein, which otherwise might show up as impurities in the final beta-casein product. While such impurities could be removed later in the process, the present inventors have found that it is both easy and convenient to do it before the second microfiltration step.

The MF-diafiltration of step c) may involve diluting the first retentate with a first diluent and subjecting the diluted first retentate to microfiltration to obtain a first diafiltration retentate and a first diafiltration permeate. The casein micelles are still retained by the MF filter while milk serum protein moves through the microfiltration filter and into the first diafiltration permeate. The dilution of retentate and subsequent microfiltration may be repeated several times, each time providing a retentate having a lower content of milk serum protein than in the previous cycle.

As will be understood, these filtration steps may be discrete steps performed one by one in a batch process or they may be performed simultaneously in a continuous process.

The use of MF-diafiltration is advantageous as it makes it possible to wash out most of the milk serum protein of the initial feed. MF-diafiltration is furthermore advantageous as it can be conducted at relatively low viscosity and therefore does not expose the casein micelles to excessive shear forces.

The MF and MF-diafiltration are typically conducted using low pressure, e.g. using a pressure of at most 5 bars, and preferably at most 4 bars. For example, the MF and MF-diafiltration may be conducted using a pressure of at most 3 bars. Alternatively, MF and MF-diafiltration may be conducted using a pressure of at most 2 bars. In preferred embodiments of the invention, the MF and MF-diafiltration are conducted using a pressure of at most 1 bar, such as e.g. at most 0.5 bar.

The filter for MF-diafiltration may be the same or similar to the one for the initial MF of the warm milk.

The temperature of the feed and subsequent retentates of the MF-diafiltration is preferably kept within the warm temperature range during at least part of the MF-diafiltration, and e.g. during the entire MF-diafiltration. This is to avoid washing out the beta-casein from the retentate during the diafiltration of step c).

In some preferred embodiments of the invention at least part of the MF-diafiltration involves the use of a first diluent having a concentration of $Ca^{2+}$ of at least 0.01 g/kg. For example, the first diluent may have a concentration of $Ca^{2+}$ of at least 0.02 g/kg. Alternatively, the first diluent may have a concentration of $Ca^{2+}$ of at least 0.04 g/kg. The first diluent may e.g. have a concentration of $Ca^{2+}$ of at least 0.1 g/kg.

The use of diluents which contain a significant amount of calcium ions seems to reduce the wash-out of beta-casein during the warm MF/MF-diafiltration step and to improve the overall yield of beta-casein of the process.

The first diluent may e.g. have a pH in the range of 5-9, and preferably in the range of 6-8. For example, the first diluent may have a pH of approx. 7. The first diluent preferably contain no or at least a very low content of protein.

In some embodiments of the invention, the first diluent comprises, or even consists of, ultrafiltration (UF) permeate of milk or whey.

Alternatively, the first diluent may be demineralised water or tap water.

The temperature used during the warm MF and MF-diafiltration, $T_{wMF}$, is at least 20 degrees C. For example, $T_{wMF}$ may be at least 30 degrees C. Alternatively, $T_{wMF}$ may be at least 40 degrees C. $T_{wMF}$ may e.g. be at least 45 degrees C.

Even higher temperatures may be desired during the warm MF and MF-diafiltration, thus, $T_{wMF}$ may be at least 50 degrees C. For example, $T_{wMF}$ may be at least 55 degrees C. Alternatively, the $T_{wMF}$ may be at least 60 degrees C.

In some embodiments of the invention, $T_{wMF}$ is in the range of 20-65 degrees C. For example, $T_{wMF}$ may be in the range of 30-60 degrees C. Alternatively, $T_{wMF}$ may be in the range of 35-55 degrees C. In some embodiments $T_{wMF}$ is in the range of 40-55 degrees C.

The duration, $t_{wMF}$, of the warm MF and the optional warm MF-diafiltration, is preferably kept as short as possible. Thus, $t_{wMF}$, is preferably at most 12 hours. For example, $t_{wMF}$ may be at most 5 hours. Alternatively, $t_{wMF}$ may be at most 2 hours. $t_{wMF}$ may be at most 1 hours. For example, $t_{wMF}$ may be at most 0.5 hours. Alternatively, $t_{wMF}$ may be at most 0.1 hours.

The retentate is preferably cooled to a temperature below 20 degrees C. when it leaves the MF-diafiltration unit or, if no diafiltration is used, when it leaves the MF unit.

As said, step d) involves adjusting the temperature of a first composition derived from the first MF retentate to a cold temperature ($T_{cold}$) in the range of 0-15 degrees C. and keeping the temperature of the first composition within that range for a duration ($t_{cold}$) of at least 0.5 hour, thereby obtaining a cooled first composition.

The first composition is preferably a liquid aqueous composition. The first composition is derived from the first MF retentate in the sense that at least 50% (w/w) of the casein micelles of the first composition originates from the first MF retentate and/or from a MF-diafiltration retentate thereof.

For example, at least 75% (w/w) of the casein micelles of the first composition may originate from the first MF retentate and/or from a MF-diafiltration retentate thereof. Preferably, at least 90% (w/w) of the casein micelles of the first composition originates from the first MF retentate and/or from a MF-diafiltration retentate thereof. Even more preferably, at least 95% (w/w) of the casein micelles of the first composition originates from the first MF retentate and/or from a MF-diafiltration retentate thereof, such as e.g. substantially all the casein micelles.

In some preferred embodiments of the invention the first composition is the first MF retentate and/or a MF-diafiltration retentate thereof.

However, in other embodiments of the invention, the first MF retentate and/or a MF-diafiltration retentate thereof may be subjected to one or more additional process steps which lead to the formation of the first composition. Such additional process steps may e.g. involve temperature adjustment, concentration, dilution, demineralisation and/or pH adjustment.

In some embodiments of the invention the provision of the first composition involves concentrating the first MF retentate and/or a MF-diafiltration retentate thereof.

In some preferred embodiments of the invention the first composition comprises a total amount of casein of at least 90% (w/w) relative to the total amount of protein of the first composition. For example, the first composition may comprise a total amount of casein of at least 92% (w/w) relative to the total amount of protein of the first composition. Alternatively, the first composition may comprise a total amount of casein of at least 94% (w/w) relative to the total amount of protein of the first composition. The first composition may e.g. comprise a total amount of casein of at least 96% (w/w) relative to the total amount of protein of the first composition, such as approx. 98 (w/w).

The first composition typically comprises a total amount of milk serum protein of at most 10% (w/w) relative to the total amount of protein of the first composition. For example, the first composition may comprise a total amount of milk serum protein of at most 8% (w/w) relative to the total amount of protein of the first composition. Alternatively, the first composition may comprise a total amount of milk serum protein of at most 6% (w/w) relative to the total amount of protein of the first composition. The first composition may e.g. comprise a total amount of milk serum protein of at most 4% (w/w) relative to the total amount of protein of the first composition.

In some embodiments of the invention the first composition comprises a total amount of protein of at least 0.1% (w/w) relative to the total weight of the first composition. For example, the first composition may comprise a total amount of protein of at least 0.5% (w/w) relative to the total weight of the first composition. The first composition may e.g. comprise a total amount of protein of at least 1% (w/w) relative to the total weight of the first composition. Alternatively, the first composition may comprise a total amount of protein of at least 2% (w/w) relative to the total weight of the first composition.

In some embodiments of the invention the first composition comprises a total amount of protein in the range of 0.1-20% (w/w) relative to the total weight of the first composition. For example, the first composition may comprise a total amount of protein in the range of 0.5-10% (w/w) relative to the total weight of the first composition. The first composition may e.g. comprise a total amount of protein in the range of 1-7% (w/w) relative to the total weight of the first composition. Alternatively, the first composition may comprise a total amount of protein in the range of 2-6% (w/w) relative to the total weight of the first composition, such as e.g. in the range of 3-4% (w/w).

In some embodiments of the invention the first composition comprises a total amount of beta-casein of at least 1% (w/w) relative to the total amount of protein. For example, the first composition may comprise a total amount of beta-casein of at least 10% (w/w) relative to the total amount of protein. The first composition may comprise a total amount of beta-casein of at least 20% (w/w) relative to the total amount of protein. Alternatively, the first composition may comprise a total amount of beta-casein of at least 30% (w/w) relative to the total amount of protein.

In some embodiments of the invention the first composition comprises a total amount of beta-casein in the range of 1-50% (w/w) relative to the total amount of protein. For example, the first composition may comprise a total amount of beta-casein in the range of 10-45% (w/w) relative to the total amount of protein. The first composition may e.g. comprise a total amount of beta-casein in the range of 20-45% (w/w) relative to the total amount of protein. Alternatively, the first composition may comprise a total amount of beta-casein in the range of 30-40% (w/w) relative to the total amount of protein.

The total amount of beta-casein may be determined according to Bobe et al (Bobe et al; 3 Agric Food Chem. 1998 Feb. 16; 46(2):458-463).

The total amount of casein may be determined according to ISO 17997-1:2004, Milk—Determination of casein-nitrogen content—Part 1: Indirect method (Reference method).

In some embodiments of the invention the first composition comprises a total amount of beta-casein of at least 20% (w/w) relative to the total amount of casein. For example, the first composition may comprise a total amount of beta-casein of at least 25% (w/w) relative to the total amount of casein. The first composition may e.g. comprise a total amount of beta-casein of at least 30% (w/w) relative to the total amount of casein. Alternatively, the first composition may comprise a total amount of beta-casein of at least 35% (w/w) relative to the total amount of casein.

In some embodiments of the invention the first composition comprises a total amount of beta-casein in the range of 20-50% (w/w) relative to the total amount of casein. For example, the first composition may comprise a total amount of beta-casein in the range of 25-45% (w/w) relative to the total amount of casein. The first composition may e.g. comprise a total amount of beta-casein in the range of 30-45% (w/w) relative to the total amount of casein. Alternatively, the first composition may comprise a total amount of beta-casein in the range of 35-40% (w/w) relative to the total amount of casein.

In some preferred embodiments of the invention, the method of the present invention comprises step c) and the first composition comprises, or even consists of, a diafiltration retentate or a protein concentrate thereof.

In the context of the present invention, a protein concentrate of a liquid contains a higher concentration of proteins than the liquid as such but substantially the same molar ratio between the individual proteins. A protein concentrate may e.g. be obtained by subjecting the liquid to ultrafiltration, reverse osmosis or solvent evaporation.

The temperature of the first composition is adjusted to a temperature, $T_{cold}$, in a cold temperature range of 0-15 degrees C. to allow casein micelle-bound beta-casein to dissociate from the casein micelles. The first composition may either be cooled directly or it may be prepared from components that have already been cooled as prescribed herein.

The cold temperature range may e.g. be 1-12 degrees C. For example, the cold temperature range may be 2-10 degrees C. The cold temperature range may e.g. be 3-7 degrees C., such as about 5 degrees C.

The first composition is preferably kept within the cold temperature range for a duration, $t_{cold}$, of at least 0.5 hour prior to step e).

In some preferred embodiments of the invention, the first composition is kept within the cold temperature range for a duration, $t_{cold}$ of at least 1 hour prior to step e). For example, $t_{cold}$ may be at least 2 hours. Alternatively, $t_{cold}$ may be at least 3 hours, such as e.g. at least 4 hours. Even longer times may be used, thus, the first composition may e.g. be kept within the cold temperature range for a duration, $t_{cold}$, of at least 15 hour prior to step e). For example, $t_{cold}$ may be at least 30 hours. Alternatively, $t_{cold}$ may be at least 60 hours, such as e.g. at least 80 hours.

The first composition may furthermore contain the usual small molecules, e.g. carbohydrates and minerals, found in mammal milk.

Step e) involves subjecting the cooled first composition to MF, thereby obtaining a second retentate and a second permeate, which second permeate is enriched with respect to beta-casein.

The second permeate is enriched with respect to beta-casein in the sense that it contains a higher weight percentage of beta-casein relative to the total amount of casein than the cooled first composition.

The microfiltration of step e) may e.g. make use of the same microfiltration system, including MF filter, which was used for the microfiltration of the warm milk.

It is preferred that the temperature of the cooled first composition and the resulting retentate is maintained within the cold temperature range during the cold MF of step e).

However, in some embodiments of the invention, the temperature of the cooled first composition is raised immediately before the second microfiltration. The present inventors have seen indications that increasing the temperature of the cooled first composition to a temperature in the range of 15-60 degrees C. immediately before the second microfiltration step has the benefit of increasing the capacity of the microfiltration unit which reducing the energy consumption of the process and this without a significant loss in the beta-casein yield. Thus, in some preferred embodiments of the invention, $T_{cold}$ is in the temperature range 0-15 degrees C. and $T_{cMF}$ is in the range of 15-60 degrees C. For example, $T_{cold}$ maybe in the temperature range 0-15 degrees C. and $T_{cMF}$ may be in the range of 15-50 degrees C. Alternatively, $T_{cold}$ maybe in the temperature range 0-15 degrees C. and $T_{cMF}$ may be in the range of 15-30 degrees C.

In the context of the present invention, the term "immediately before the second microfiltration" means at most 10 minutes before the first composition contacts the membrane of the filtration unit performing the second microfiltration, preferably at most 5 minutes before, and even more preferred at most 2 minutes before, such as at most 1 minute before.

In some preferred embodiments of the invention the method comprises step f), i.e. a step of subjecting the second retentate to MF-diafiltration in order to wash out more beta-casein.

The present inventors have found that it is advantageous to perform diafiltration after the second microfiltration step as it allows for washing out more beta-casein from the second MF retentate, and thereby increasing the beta-casein yield per kg milk feed.

The MF-diafiltration of step f) may involve diluting the second retentate with a second diluent and subjecting the diluted second retentate to microfiltration to obtain a diafiltration retentate and a diafiltration permeate. The casein micelles are still retained by the MF filter while dissociated beta-casein moves through the microfiltration filter and into the diafiltration permeate. The dilution of diafiltration retentate and subsequent microfiltration may be repeated several times, each time providing a retentate having a lower content of beta-casein than in the previous cycle.

The second diluent typically has a pH in the range of 5-9, and preferably in the range of 6-8. For example, the second diluent may have a pH of approx. 7. The second diluent preferably contain no or only a very low content of protein.

In some embodiments of the invention, the second diluent comprises, or even consists of, ultrafiltration (UF) permeate of milk or whey.

Alternatively, the second diluent may be demineralised water or tap water. The present inventors have seen indications that the use of water as the second diluent in the second MF-diafiltration step increases the amount beta-casein that is released from the casein micelles during the second MF-diafiltration and thus seems to increase the over-all yield of beta-casein per kg milk feed.

The diafiltration permeate(s) of step f) contain free beta-casein and may be pooled with the second permeate.

The second permeate or the pooled second permeate and subsequent cold MF-diafiltration permeates may be used as the beta-casein composition of the invention.

It is preferred that the temperature of the retentates is maintained within the cold temperature range during the cold MF of step e) and also during the cold MF-diafiltration of step f) if the latter is included in the process.

The cold MF and cold MF-diafiltration are typically conducted using low pressure, e.g. using a pressure of at most 5 bars, and preferably at most 4 bars. For example, the MF and MF-diafiltration may be conducted using a pressure of at most 3 bars. Alternatively, MF and MF-diafiltration may be conducted using a pressure of at most 2 bars. The MF and MF-diafiltration may e.g. be conducted using a pressure of at most 1 bar, such as e.g. at most 0.5 bar.

The duration, $t_{cMF}$, of the cold MF and the optional cold MF-diafiltration, is preferably kept as short as possible. Thus, $t_{cMF}$, is preferably at most 12 hours. For example, $t_{cMF}$ may be at most 5 hours. Alternatively, $t_{cMF}$ may be at most 2 hours. $t_{cMF}$ may be at most 1 hours. For example, $t_{cMF}$ may be at most 0.5 hours. Alternatively, $t_{cMF}$ may be at most 0.1 hours.

In some preferred embodiments of the invention, the method contains a step g) of subjecting a second composition derived from the second permeate to one or more further processing steps, e.g. further purification and/or concentration steps.

The second composition is preferably a liquid aqueous composition. The second composition is derived from the second MF permeate in the sense that at least 50% (w/w) of the beta-casein of the second composition originate from the second MF permeate and/or further permeate(s) obtained from step f).

For example, at least 75% (w/w) of the beta-casein of the second composition may originate from the second MF permeate and/or further permeate(s) obtained from the MF-diafiltration of step f). Preferably, at least 90% (w/w) of the beta-casein of the second composition originate from the second MF permeate and/or a further permeate(s) obtained from the MF-diafiltration of step f). Even more preferably, at least 95% (w/w) of the beta-casein of the second composition originate from the second MF permeate and/or a further permeate(s) obtained from the MF-diafiltration of step f), such as e.g. substantially all the beta-casein.

In some preferred embodiments of the invention the second composition is the second MF permeate and/or a further permeate(s) obtained from the MF-diafiltration of step f). Alternatively, the second composition may be a protein concentrate of the second MF permeate and/or a further permeate(s) obtained from the MF-diafiltration of step f).

However, in other embodiments of the invention, the second MF permeate and/or a further permeate(s) obtained from the MF-diafiltration of step f) may be subjected to additional process steps which lead to the formation of the second composition. Such additional process steps may e.g. involve temperature adjustment, concentration, dilution, demineralisation, and/or pH adjustment.

In some embodiments of the invention the provision of the second composition involves concentrating the second MF permeate and/or a further permeate(s) obtained from the MF-diafiltration of step f).

In some embodiments of the invention the concentration of step g) involves heating the second composition to a temperature and for a duration sufficient for the formation of beta-casein sub-micelles and subsequently subjecting the second composition containing the beta-casein sub-micelles to ultrafiltration microfiltration under conditions which retain the beta-casein sub-micelles in the retentate and allows for the passage of serum proteins into the permeate.

The nominal molecular weight cut-off of the membrane used for the ultrafiltration may e.g. be in the range of 50-750 kDa, and preferably in the range of 75-400 kDa, such as e.g. in the range of 100-300 kDa.

In some embodiments of the invention the concentration of step g) increases the weight percentage of beta-casein of the second composition to at least 50% (w/w) on a dry weight basis.

In some embodiments of the invention the concentration of step g) increases the weight percentage of beta-casein in the second composition to 50-85% (w/w) on a dry weight basis.

In some embodiments of the invention the concentration of step g) increases the solids content of the second composition to at least 5% (w/w). For example, the concentration of step g) may increase the solids content of the second composition to at least 10% (w/w). Alternatively, the concentration of step g) may increases the solids content of the second composition to at least 15% (w/w), such as at least 20% (w/w).

The concentration of step g) may e.g. involve one or more processes selected from the group consisting of ultrafiltration, nanofiltration, reverse osmosis, evaporation, spray drying and freeze drying. For example, the concentration of step g) may e.g. involve two or more processes selected from the group consisting of ultrafiltration, nanofiltration, reverse osmosis, evaporation, spray drying, and freeze drying.

The present method may e.g. be implemented as a batch method or as a continuous method. Each step may be implemented as a discrete batch. Alternatively, groups of steps may be implemented as a continuous sub-process. For example, steps b) and c) may be implemented as a continuous sub-process. Alternatively, or additionally, steps e) and f) may be implemented as a continuous sub-process.

The MF systems used in the MF and/or MF-diafiltration steps are preferably systems that allow for controlling the temperature of the feed and retentate stream, e.g. by water-heating or water-cooling.

Figure 2:
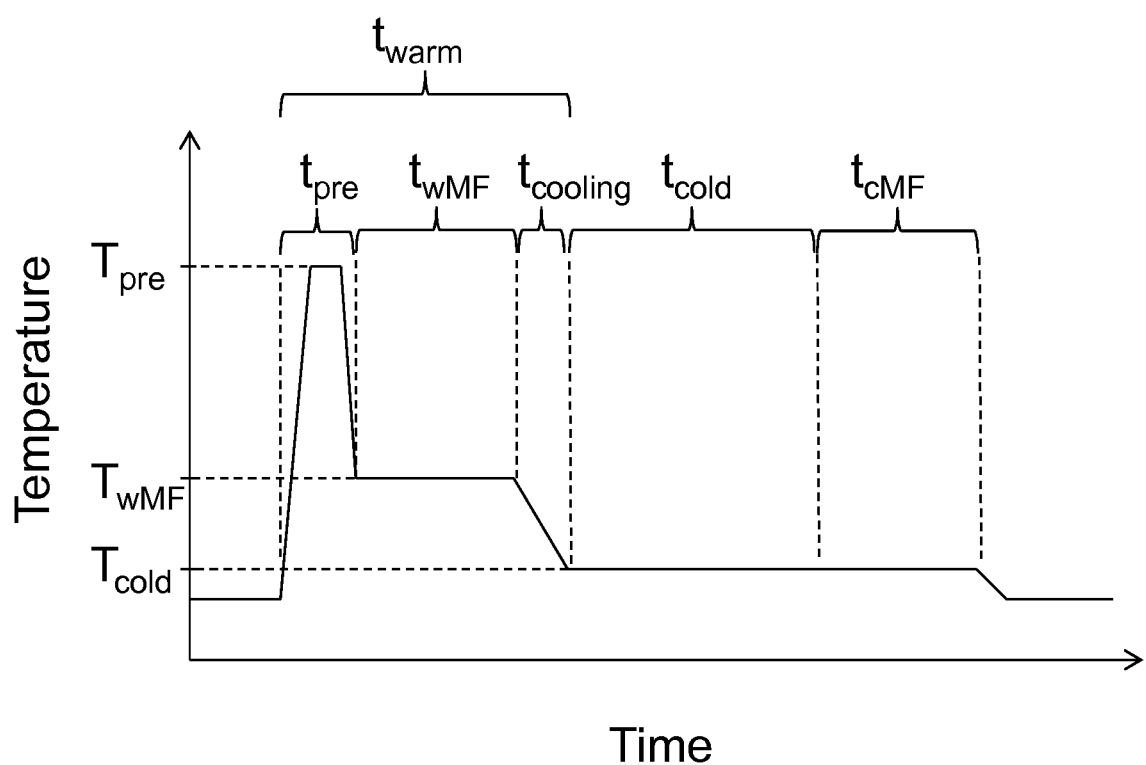
FIG. 2 illustrates the temperature profile of a method which includes a high pre-heating temperature, $T_{pre}$, and a somewhat lower temperature during the microfiltration of the warm milk, $T_{wMF}$.
Figure 3:
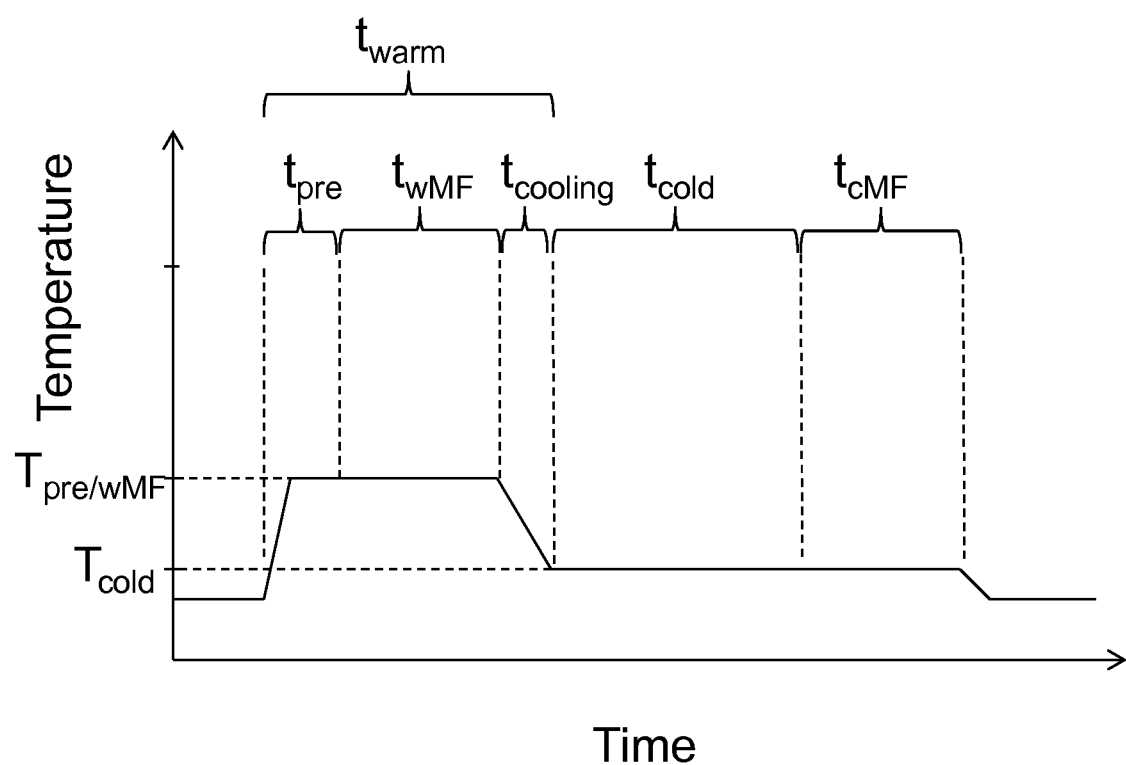
FIG. 3 illustrates the temperature profile of a method wherein $T_{pre}$ is approximately the same as $T_{wMF}$.

It is preferred to control both the temperature and the duration of various steps of the method. FIGS. 2 and 3 illustrate two non-limiting examples the timing and temperature profile during such a method.

The symbols used in FIGS. 2 and 3 have the following meaning:

$T_{pre}$=The temperature to which the milk is heated during the pre-heating.

$t_{pre}$=The duration for which the milk is held within the desired interval of $T_{pre}$ during the pre-heating.

$T_{wMF}$=The temperature of the milk during the warm MF. If the warm MF is followed by warm MF-diafiltration, the temperature of the retentate stream is preferably also $T_{wMF}$ or within the desired interval for $T_{wMF}$.

$t_{wMF}$=The duration of the warm MF. If the warm MF is followed by warm MF-diafiltration, $t_{wMF}$ is the combined duration of the warm MF and the warm MF-diafiltration.

$t_{warm}$=The average amount of time during the process that a casein micelle is kept at a temperature of at least 20 degrees C.

$t_{cooling}$=The duration of cooling the retentate from $T_{wMF}$ to a temperature within the desired interval for $T_{cold}$.

$T_{cold}$=The temperature of the first composition during the cold storage step and during the cold MF/MF-diafiltration.

$t_{cold}$=The duration of the cold storage step.

$t_{cMF}$=The duration of the cold MF/MF-diafiltration.

If the method is implemented as a continuous process, the durations related to the processing or specific conditions of the milk or the casein-micelle-containing retentates are the average time that a casein-micelle is subjected to the mentioned processing or specific condition.

FIG. 2 differs from FIG. 3 in that it has a $T_{pre}$ which is significantly higher than the $T_{wMF}$. In the method according to FIG. 3, $T_{pre}$ is approximately the same as $T_{wMF}$.

The use of a short pre-heating at a relatively high pre-heating temperature followed by a warm MF/MF-diafiltration at lower $T_{wMF}$ represents an interesting embodiment as it seems to reduce the digestion of beta-casein caused by plasmin.

While it is preferred that the method of the present invention is implemented with tight control of temperature and timing, some fluctuation of the temperature may be acceptable, as long as $T_{pre}$, $T_{wMF}$, $T_{cold}$ stay within the intervals mentioned herein.

It is preferred that the time which the milk and the related casein-micelle-containing streams are held at high temperature is kept at a minimum. Thus, in some embodiments of the invention the average time, $t_{warm}$, a casein-micelle is kept at a temperature of at least 20 degrees C. is at most 6 hours.

For example, the average time, $t_{warm}$, a casein-micelle is kept at a temperature of at least 20 degrees C. may be at most 3 hours. The average time, $t_{warm}$, a casein-micelle is kept at a temperature of at least 20 degrees C. may e.g. be at most 1 hour. Alternatively, the average time, $t_{warm}$, a casein-micelle is kept at a temperature of at least 20 degrees C. may be at most 0.5 hours. Even faster processing is possible, thus, the average time, $t_{warm}$, a casein-micelle is kept at a temperature of at least 20 degrees C. may be at most 0.1 hour.

Reducing the average time at high temperature seems to reduce the level of plasmin digestion of beta-casein thereby improving the yield of beta-casein.

In some preferred embodiments of the invention, the retentate resulting from steps b) or c) is subjected to a plasmin inactivation step, such as e.g. a heat inactivation step. The heat inactivation step may for example involve adjusting the temperature of the retentate to a temperature in the range of 70-100 degrees C. and keeping the temperature of the milk-related feed in that range for a period in the range of 10-500 seconds. The heat inactivation step may for example involve adjusting the temperature of the retentate to a temperature in the range of 85-95 degrees C. and keeping the temperature of the milk-related feed in that range for a period in the range of 10-100 seconds.

It seems particularly advantageous to inactivate plasmin after milk serum proteins have been at least partly removed by the warm MF/MF-diafiltration, as the milk serum proteins are more prone to thermal denaturation than the caseins.

The inactivation of plasmin also results in reducing the level of plasmin digestion of beta-casein and thereby improves the yield of beta-casein.

The casein-containing streams, e.g. the milk and the subsequent casein-containing retentates, typically have a pH in the range of 6-8, and preferably a pH in the range of 6.5-7.5. pH values mentioned herein are measured at 25 degrees C. unless stated otherwise.

A further aspect of the invention pertains to a method of producing a beta-casein-containing composition, and optionally also a serum protein fraction and a beta-casein reduced MCI fraction, the method comprising the steps of:

1) Providing a cooled casein micelle-containing composition,
2) subjecting the cooled casein micelle-containing composition to microfiltration (MF), thereby obtaining a casein micelle-containing retentate and a beta-casein enriched permeate,
3) optionally, subjecting the casein micelle-containing retentate to MF-diafiltration, and
4) optionally, subjecting a third composition derived from the beta-casein enriched permeate to one or more further processing steps, thereby providing the beta-casein-containing composition.

The beta-casein-containing composition may e.g. be the third permeate of step 2) or the purified and/or concentrated product resulting from step 3).

Step 1) provides a cooled casein micelle-containing composition. The cooled casein micelle-containing composition preferably has one or more of the characteristics described in the context of the cooled first composition. The cooled casein micelle-containing composition may have been prepared according to the steps a)-d) described herein. Alternatively, the cooled casein micelle-containing composition may e.g. have been prepared by resuspending a dried micellar casein isolate in a first diluent and subjecting the resuspended micellar casein isolate to cooling as described in the step d).

Step 2) involves subjecting the cooled casein micelle-containing composition to microfiltration (MF), thereby obtaining a casein micelle-containing retentate and a beta-casein enriched permeate. This step e) could be a step like step e) and results in a permeate enriched with respect to beta-casein Step 3) is optional, yet preferred, and involves subjecting the casein micelle-containing retentate to MF-diafiltration. Step 3) may have any of the characteristics described in the context of step f).

Step 4) involves subjecting a third composition derived from the beta-casein enriched permeate to one or more further processing steps, e.g. further purification and/or concentration steps. Step 4) may have any of the characteristics described in the context of step g).

Yet an aspect of the invention pertains to a beta-casein-containing composition obtainable by a method according to any of the preceding claims.

As stated above, the beta-casein-containing composition of the invention preferably contains at least 30% (w/w) beta-casein relative to the total amount of protein. For example, the beta-casein-containing composition may contain at least 50% (w/w) beta-casein relative to the total amount of protein. The beta-casein-containing composition may contain at least 60% (w/w) beta-casein relative to the total amount of protein. Alternatively, the beta-casein-containing composition may contain at least 70% (w/w) beta-casein relative to the total amount of protein, such as e.g. at least 80% (w/w) beta-casein.

In some preferred embodiments of the invention, the beta-casein-containing composition contains an amount of beta-casein in the range of 30-100% (w/w) relative to the total amount of protein. For example, the beta-casein-containing composition may contain an amount of beta-casein in the range of 50-95% (w/w) relative to the total amount of protein. The beta-casein-containing composition may e.g. contain an amount of beta-casein in the range of 55-90% (w/w) relative to the total amount of protein. Alternatively, the beta-casein-containing composition may contain an amount of beta-casein in the range of 60-80% (w/w) relative to the total amount of protein.

The beta-casein containing composition of the invention preferably contains at least 50% (w/w) beta-casein relative to the total amount of casein. For example, the beta-casein-containing composition may contain at least 70% (w/w) beta-casein relative to the total amount of casein. The beta-casein-containing composition may contain at least 80% (w/w) beta-casein relative to the total amount of casein. Alternatively, the beta-casein-containing composition may contain at least 90% (w/w) beta-casein relative to the total amount of casein. For example, the beta-casein-containing composition may contain at least 95% (w/w) beta-casein relative to the total amount of casein, such as e.g. at least 97% (w/w) beta-casein.

The present invention has been described above with reference to specific embodiments. However, other embodiments than the above described are equally possible within the scope of the invention. The different features and steps of various embodiments and aspects of the invention may be combined in other ways than those described herein unless it is stated otherwise.

EXAMPLES

Example 1

Production of Beta-Casein According to the Invention

A beta-casein isolate was produced according to the method of the present invention.

Warm Microfiltration/MF-Diafiltration:

25 m$^3$ of cooled non-pasteurised skimmed milk was pre-heated to 55 degrees C. for 10 minutes in a heat-and-hold tank and subjected to continuous microfiltration using 6" spiral wound membranes of the type FR6338 from Synder Filtration, Vacaville, Calif., US, with 46 mil spacer and a nominal cut-off value of 800,000 Daltons. The feed flow rate was 4000 L/h. Four loops were present in the continuous microfiltration equipment. The total membrane area was 1208 m$^2$. The filtration was carried out under the following conditions: The skimmed milk was concentrated with a concentration factor of 1.3. The temperature was maintained at 50 degrees C., and the mean pressure was maintained at 0.53 bar across two filter elements with a feeding pressure of 0.15 bar. The permeate from the microfiltration was directed to a parallel ultrafiltration process, and the permeate from the ultrafiltration process was continuously directed back to the microfiltration retentate in order to carry out diafiltration of the microfiltration retentate. 287% diafiltration was carried out, i.e. the volume of ultrafiltration permeate used for diafiltration was 2.87 times the volume of the skimmed milk supplied to the microfiltration process. The mean flux was approximately 17 L/m$^2$/h. The processed microfiltration retentate was continuously subjected to heat treatment at 74 degrees C. for 15 seconds, cooled down to 6 degrees C. and collected in a tank. A total of 18 m$^3$ of MCI (micellar casein isolate) solution was collected at the end of the microfiltration process. The protein content in the MCI solution was 4.1% (gram protein per 100 gram solution).

Ultrafiltration of the Permeate from the Warm Microfiltration:

The permeate from the microfiltration process was collected in a feed tank to the continuous ultrafiltration process. Simultaneously with the microfiltration process, ultrafiltration was carried out using 6" spiral wound membranes of the type HFK-328 6338 from Koch Membrane Systems, Wilmington, Mass., US, with 31 mil spacer and a nominal cut-off value of 5,000 Daltons. Two loops were present in the continuous ultrafiltration equipment. The total membrane area was 528 m$^2$. The filtration was carried out under the following conditions: The temperature was maintained at 50 degrees C., and the mean pressure was maintained at 2.8 to 3.5 bars across three filter elements in order to supply ultrafiltration permeate to the microfiltration process with the same flow as microfiltration permeate was removed from the microfiltration process. The mean flux was approximately 30 L/m$^2$/h.

Storage of MCI Solution:

The MCI solution was stored at 6 degrees C. for a period of 60 hours.

Cold Microfiltration of the MCI Solution:

1200 litres of the stored MCI solution was subjected to microfiltration using 6" spiral wound membranes of the type FR6338 from Synder Filtration, Vacaville, Calif., US, with 46 mil spacer and a nominal cut-off value of 800,000 Daltons.

The total membrane area was 382 m$^2$. The filtration was carried out under the following conditions: The temperature was maintained at approximately 6 degrees C., and the mean pressure was maintained at 0.40 bar across two filter elements with a feeding pressure of 0.05 bar. The permeate from the microfiltration was directed to a parallel ultrafiltration process, and the permeate from the ultrafiltration process was continuously directed back to the microfiltration retentate in order to carry out diafiltration of the microfiltration retentate. 500% diafiltration was carried out, i.e. the volume of ultrafiltration permeate used for diafiltration was five times the volume of the MCI solution supplied to the microfiltration process. The mean flux was measured as 5.0 L/m$^2$/h.

Concentration of the Permeate of the Cold MF by Ultrafiltration:

The permeate from the cold microfiltration process was collected in a feed tank to the ultrafiltration process. Simultaneously with the cold microfiltration process, ultrafiltration was carried out using 6" spiral wound membranes of the type HFK-328 6338 from Koch Membrane Systems, Wilmington, Mass., US, with 31 mil spacer and a nominal cut-off value of 5,000 Daltons. The total membrane area was 176 m$^2$. The filtration was carried out under the following conditions: The temperature was maintained at approximately 6 degrees C., and the mean pressure was maintained at 1.5 to 3.0 bars across two filter elements in order to supply ultrafiltration permeate to the microfiltration process with the same flow as microfiltration permeate was removed from the microfiltration process. The mean flux was approximately 11 L/m$^2$/h. When the filtration process was completed after 3 hours, approximately 400 litres of ultrafiltration retentate was collected. The retentate was subsequently subjected to diafiltration in which 3,000 litres of tap water was added with the same flow as filtrate was removed, in order to remove lactose. After the diafiltration the retentate was concentrated until the protein content in the retentate was 3%. The final volume of the retentate was 150 litres. The filtration conditions were the same as above.

Pasteurisation and spray-drying of the beta-casein-containing UF-permeate: Approximately 70 litres of the final retentate from the cold ultrafiltration was subjected to pasteurisation at 72 degrees C. for 15 seconds. After pasteurisation a one-stage spray drying of the protein solution was carried out using standard parameters including an air inlet temperature of 180 degrees C. and an air outlet temperature of 90 degrees C. 2.1 kg of powder was obtained.

The content of protein in the powder was measured as 91% (gram protein per 100 gram powder), and the content of dry matter in the powder was measured as 95% (gram dry matter per 100 gram powder). The beta-casein content of the powder was analysed as described in Example 3 and determined to 75% (gram beta-casein per 100 gram protein).

The content of the amino acid proline was analysed according to Example 3 and determined to 13.0 gram proline per 100 gram protein.

Example 2

Production of Beta-Casein According to the Invention

Another beta-casein isolate was produced according to the method of the present invention.
Warm Microfiltration/MF-Diafiltration:

Pre-treatment and microfiltration of cooled pasteurised skimmed milk was carried out essentially as described in Example 1, except for the following: 35 m$^3$ of skimmed milk was used, and the skimmed milk was pre-heated to 55 degrees C. for 7 minutes in a heat-and-hold tank. Both 6" and 8" spiral wound membranes were used, and five loops were present in the continuous microfiltration equipment. The total membrane area was 1399 m$^2$. The feed flow rate was 5000 L/h. The mean pressure was maintained at 0.53 bar across two filter elements with a feeding pressure of 0.15 bar. 327% diafiltration was carried out, i.e. the volume of ultrafiltration permeate used for diafiltration was 3.27 times the volume of the skimmed milk supplied to the microfiltration process. The mean flux was measured as 16 L/m$^2$/h. A total of 27 m$^3$ of MCI (micellar casein isolate) solution was collected at the end of the microfiltration process. The protein content in the MCI solution was 4.6% (gram protein per 100 gram solution).
Ultrafiltration of the Permeate from the Warm Microfiltration:

The ultrafiltration process was carried out essentially as described in Example 1 except for the following: Membranes with 31 mil, 46 mil and 80 mil spacer were used. Four loops were present in the continuous ultrafiltration equipment. The total membrane area was 1331 m$^2$. The mean flux was approximately 15 L/m$^2$/h.
Storage of MCI Solution:

The MCI solution was stored at 5 degrees C. for a period of 29 hours.
Cold Microfiltration of the Micellar Casein Isolate:

The 27 m$^3$ of stored MCI solution was subjected to continuous microfiltration using 6" and 8" spiral wound membranes of the type FR6338 from Synder Filtration, Vacaville, Calif., US, with 46 mil spacer and a nominal cut-off value of 800,000 Daltons. Five loops were present in the continuous microfiltration equipment. The total membrane area was 1399 m$^2$. The filtration was carried out under the following conditions: The temperature was maintained at 7 degrees C., and the mean pressure was maintained at 0.58 bar across two filter elements with a feeding pressure of 0.15 bar. The permeate from the microfiltration was directed to a parallel ultrafiltration process, and the permeate from the ultrafiltration process was continuously directed back to the microfiltration retentate in order to carry out diafiltration of the microfiltration retentate. 469% diafiltration was carried out, i.e. the volume of ultrafiltration permeate used for diafiltration was 4.69 times the volume of the MCI solution supplied to the microfiltration process. The mean flux was approximately 8 L/m$^2$/h. The processed microfiltration retentate was continuously collected in a tank.
Concentration of the Permeate of the Cold MF by Ultrafiltration:

The permeate from the microfiltration process was collected in a feed tank to the continuous ultrafiltration process. Simultaneously with the microfiltration process, ultrafiltration was carried out using 6" spiral wound membranes of the type HFK-328 6338 from Koch Membrane Systems, Wilmington, Mass., US, with 31, 46 and 80 mil spacer and a nominal cut-off value of 5,000 Daltons. Four loops were present in the continuous ultrafiltration equipment. The total membrane area was 1331 m$^2$. The filtration was carried out under the following conditions: The temperature was maintained at 7 degrees C., and the mean pressure was maintained at 2.0 to 5.0 bars across three filter elements in order to supply ultrafiltration permeate to the microfiltration process with the same flow as microfiltration permeate was removed from the microfiltration process. Continuously the retentate from the ultrafiltration process was subjected to diafiltration using demineralised water. The mean flux was approximately 15 L/m$^2$/h. At the end of the filtration, 1400 litres of ultrafiltration retentate was collected.
Pasteurisation and Spray-Drying of the Beta-Casein-Containing UF-Permeate:

The 1400 litres of ultrafiltration retentate was concentrated by reverse osmosis (RO) using standard operating conditions. 880 litres of RO concentrate was obtained, and the protein content in the RO retentate was 12%. The RO retentate was subjected to pasteurisation at 72 degrees C. for 15 seconds. After pasteurisation, a one-stage spray drying of the protein solution was carried out using standard parameters including an air inlet temperature of 180 degrees C. and an air outlet temperature of 88 degrees C. 125 kg of powder was obtained.

The content of protein in the powder was measured as 83% (gram protein per 100 gram powder), and the content of dry matter in the powder was measured as 96% (gram dry matter per 100 gram powder). The beta-casein content of the powder was analyse as described in Example 3 and determined to 76% (gram beta-casein per 100 gram protein).

Example 3

Analysis of Beta-Casein Purity and Amino Acid Profile

Determination of Beta-Casein Purity

The purity of beta-casein in powdered products was determined by Reversed Phase HPLC as outlined by Bobe et al. using a C18 column from Waters Corporation, Milford, Mass., US, and a water/acetonitrile solvent system. Prior to the analysis the sample is dissolved in 6 M urea and 20 mM dithiothreitol with the purpose of obtaining a denatured and reduced protein solution.
Determination of Amino Acid Profile The amino acid profile of the powdered products was analysed by standard amino acid analysis.

Example 4

Analysis by Capillary Electrophoresis and Comparison with the Prior Art

The beta-casein enriched powder produced in Example 1 was compared to a commercially available beta-casein product. This comparison was carried out by means of analysing the two products by capillary electrophoresis.

Figure 4:
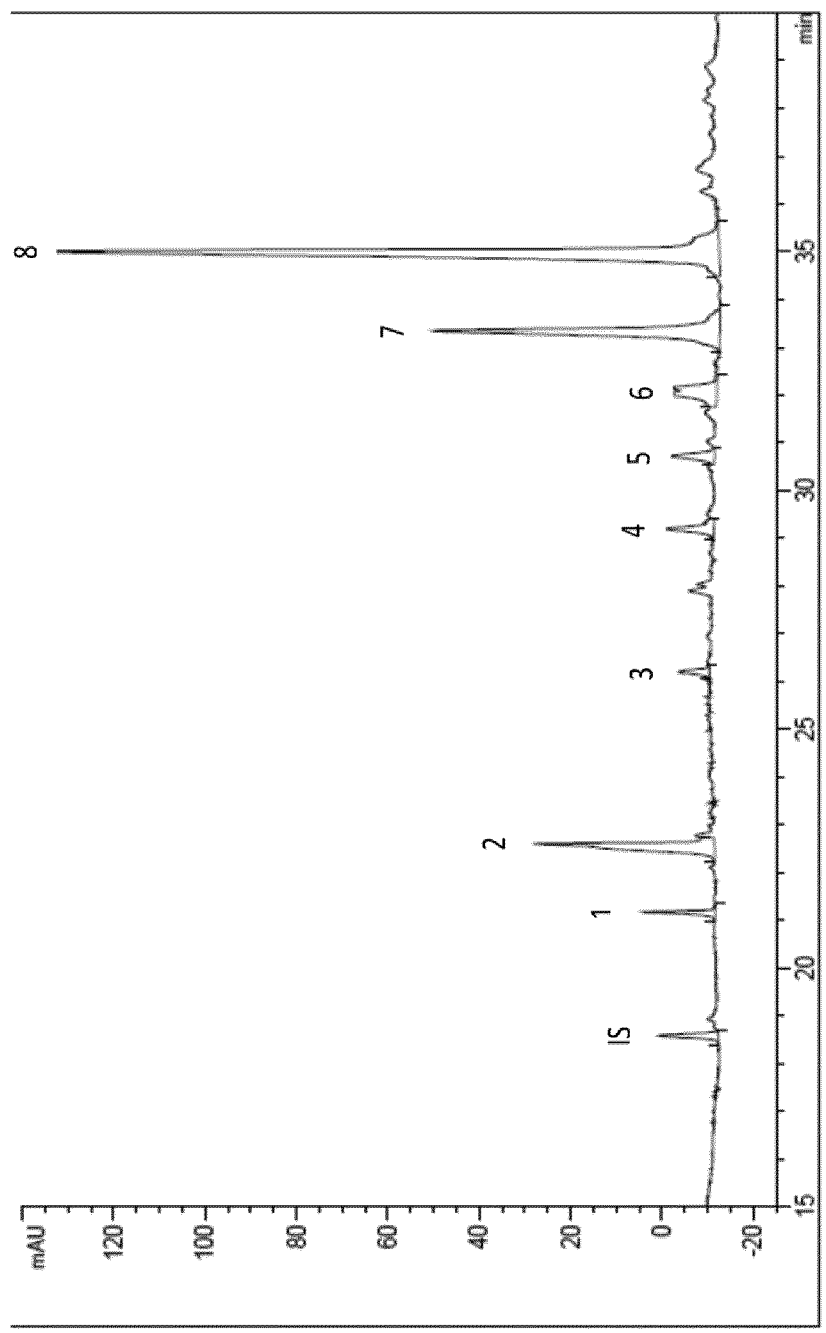
FIG. 4 is an electropherogram from capillary electrophoresis analysis of the beta-casein-containing composition obtained as described in Example 1.
Figure 5:
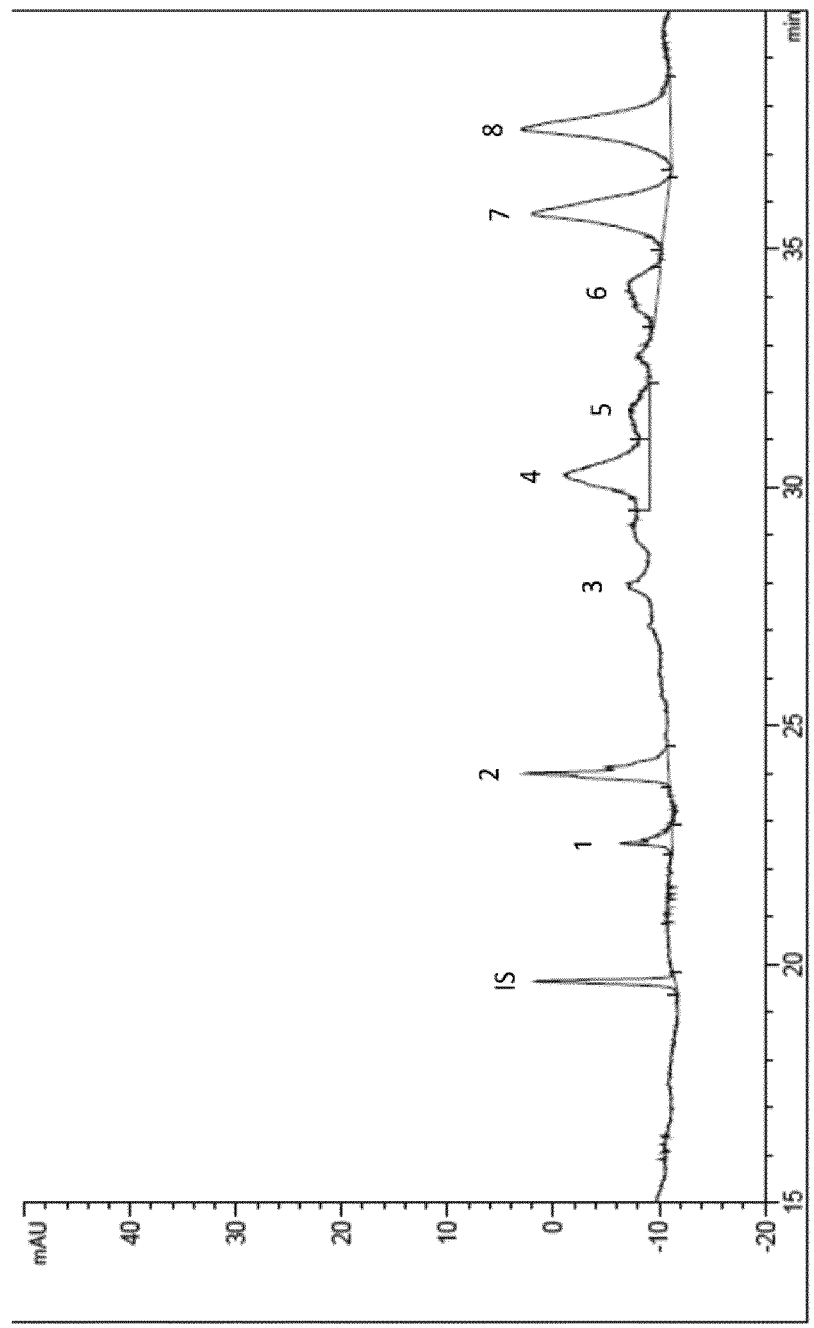
FIG. 5 is an electropherogram from capillary electrophoresis analysis of a commercially available beta-casein preparation.

The obtained electropherograms are shown in FIG. 4 (product of Example 1) and FIG. 5 (prior art product), and the individual known peaks are denominated in Table 1.

TABLE 1

Denomination of peaks in FIGS. 4 and 5.

| Peak ID | Component |
|---|---|
| IS | Internal standard |
| 1 | Alpha-lactalbumin |
| 2 | Beta-lactoglobulin |
| 3 | Alpha-S2-casein |
| 4 | Alpha-S1-casein (variant 1) |
| 5 | Alpha-S1-casein (variant 2) |
| 6 | Beta-casein (variant 1) |
| 7 | Beta-casein (variant 2) |
| 8 | Beta-casein (variant 3) |

In general, the peaks in the electropherogram for the commercially available product are much broader than the peaks in the electropherogram for the product of Example 1. This demonstrates that a significant modification of the proteins in the commercially available product has occurred. The peaks in the electropherogram for the product of Example 1 are sharp, which demonstrates no or only an insignificant degree of modification. Further, the ratio of other caseins vs beta-casein is much larger for the commercially available product compared to the product of Example 1, indicated by the large peak for alpha-S1-casein (variant 1) in the electropherogram for the commercially available product.

The invention claimed is:

1. A method of producing a beta-casein-containing composition, the method comprising the steps of:
   a) pre-heating a milk by adjusting it to a pre-heating temperature in the range of 20-60 degrees C. and with a holding time in the range of 1 minute-1 hour, thereby providing a warm milk,
   b) subjecting the warm milk to a first microfiltration at a first microfiltration temperature using a filter that retains at least a substantial fraction of casein micelles but allows for the passage of milk serum protein, thereby providing a first microfiltration permeate and a first microfiltration retentate,
   c) subjecting the first microfiltration retentate to a first microfiltration-diafiltration at a first microfiltration-diafiltration temperature, wherein (i) at least part of the microfiltration-diafiltration involves the use of a first diluent having $Ca^{2+}$ concentration of at least 0.01 g/kg, and (ii) the first microfiltration retentate comprises at least 92% (w/w) casein relative to the total amount of protein of the first microfiltration retentate;
   d) adjusting the temperature of the first microfiltration retentate to a cold temperature in the range of 0-15 degrees C. and keeping the temperature of the first microfiltration retentate within that range for a duration of at least 0.5 hour, thereby obtaining a cooled first composition,
   e) subjecting the cooled first composition to a second microfiltration, thereby obtaining a second microfiltration retentate and a second microfiltration permeate, which second microfiltration permeate is enriched with respect to beta-casein,
   f) optionally, subjecting the second microfiltration retentate to a second microfiltration-diafiltration, and
   g) optionally, subjecting the second microfiltration permeate to one or more further purification or concentration steps, thereby providing the beta-casein-containing composition.

2. The method according to claim 1, wherein the filter for microfiltration of the warm milk has a nominal pore size in the range of 0.005-0.3 micrometer.

3. The method according to claim 1, wherein the first microfiltration temperature of step b) is at least 20 degrees C.

4. The method according to claim 1, wherein the filter for the first microfiltration-diafiltration is the same or similar to the one for the first microfiltration of step b).

5. The method according to claim 1, wherein the first microfiltration-diafiltration temperature is kept within the range of the first microfiltration temperature of step b) during at least part of the first microfiltration-diafiltration.

6. The method according to claim 1, wherein the first diluent has a pH in the range of 6-8.

7. The method according to claim 1, wherein the first diluent comprises ultrafiltration permeate of milk or whey.

8. The method according to claim 1, wherein the first microfiltration retentate comprises a total amount of protein of at least 0.1% (w/w) relative to the total weight of the first microfiltration retentate.

9. The method according to claim 1, wherein the first microfiltration retentate comprises a total amount of beta-casein of at least 0.1% (w/w) relative to the total amount of protein.

10. The method according to claim 1, wherein the first microfiltration retentate comprises a total amount of beta-casein of at least 20% (w/w) relative to the total amount of casein.

11. The method according to claim 1, which comprises subjecting the first microfiltration retentate to a first microfiltration-diafiltration at a first microfiltration-diafiltration temperature, and wherein the first microfiltration retentate comprises a diafiltration retentate or a protein concentrate thereof.

12. The method according to claim 1, wherein the first microfiltration retentate is kept within the cold temperature range for at least 1 hour prior to step e).

13. The method according to claim 1, wherein the cooled first composition has a temperature in the range of 3-12 degrees C.

14. The method according to claim 1, wherein the second microfiltration of step e) uses the same microfiltration filter as that used in the first microfiltration of step b).

15. The method according to claim 1, which comprises subjecting the second microfiltration retentate to a second microfiltration-diafiltration.

16. The method according to claim 1, which comprises subjecting the second microfiltration permeate to one or more further purification or concentration steps.

17. The method according to claim 16, which comprises increasing the weight percentage of beta-casein of the second microfiltration permeate to at least 50% (w/w) on a dry weight basis.

18. The method according to claim 16, which comprises increasing the weight percentage of beta-casein in the second microfiltration permeate to 50-85% (w/w) on a dry weight basis.

19. The method according to claim 16, which comprises increasing the solids content of the second microfiltration permeate to at least 5% (w/w).

20. The method according to claim 16, wherein the one or more concentration steps comprises ultrafiltration, nanofiltration, reverse osmosis, evaporation, spray drying, and/or freeze drying.

* * * * *